(12) United States Patent
Igarashi

(10) Patent No.: US 11,590,268 B2
(45) Date of Patent: Feb. 28, 2023

(54) BLOOD COMPONENT COLLECTION CASSETTE AND MANUFACTURING METHOD OF THE SAME

(71) Applicant: TERUMO KABUSHIKI KAISHA, Tokyo (JP)

(72) Inventor: Masatsugu Igarashi, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 541 days.

(21) Appl. No.: 16/496,341

(22) PCT Filed: Mar. 20, 2018

(86) PCT No.: PCT/JP2018/011131
§ 371 (c)(1),
(2) Date: Sep. 20, 2019

(87) PCT Pub. No.: WO2018/174074
PCT Pub. Date: Sep. 27, 2018

(65) Prior Publication Data
US 2020/0030505 A1    Jan. 30, 2020

(30) Foreign Application Priority Data
Mar. 23, 2017 (JP) .............................. JP2017-057687

(51) Int. Cl.
*A61M 1/02* (2006.01)
*A61M 1/36* (2006.01)
(Continued)

(52) U.S. Cl.
CPC .......... *A61M 1/0222* (2014.02); *A61M 1/025* (2013.01); *A61M 1/3672* (2013.01);
(Continued)

(58) Field of Classification Search
CPC ...... A61M 1/0222; A61M 1/025; A61M 1/30; A61M 1/3496; A61M 1/3672; A61M 1/38;
(Continued)

(56) References Cited

U.S. PATENT DOCUMENTS 6,270,673 B1 *   8/2001   Belt ..................... A61M 1/3451
                                                              210/646
6,481,980 B1 *  11/2002   Vandlik ................. A61M 1/30
                                                              417/313
(Continued)

FOREIGN PATENT DOCUMENTS

EP        2476447 A1      7/2012
JP        H11-216179      8/1999
(Continued)

OTHER PUBLICATIONS

Official Action (with translation) for Japan Patent Application No. 2019-543868, dated Nov. 30, 2021, 8 pages.
(Continued)

*Primary Examiner* — Dirk R Bass
(74) *Attorney, Agent, or Firm* — Sheridan Ross P.C.

(57) ABSTRACT

A blood component collection cassette that can trap a substance where blood components coagulate by using a simple and economical configuration, and a manufacturing method of the blood component collection cassette are provided.
A blood component collection cassette (28) includes a cassette main body (40) where a flow path (42) is formed and is configured to be mountable to a centrifugal separation device (14). The cassette main body (40) has a first sheet (40*a*) and a second sheet (40*b*) which are formed of a soft material. The flow path (42) is formed between the first sheet (40*a*) and the second sheet (40*b*). A filter member (60) for
(Continued)

trapping a substance where blood components coagulate is arranged on the flow path (42) in the cassette main body (40).

20 Claims, 8 Drawing Sheets

(51) Int. Cl.
*B01D 29/11* (2006.01)
*B01D 29/35* (2006.01)
*B29C 49/20* (2006.01)
B04B 5/04 (2006.01)
B29L 31/00 (2006.01)

(52) U.S. Cl.
CPC ............ *B01D 29/111* (2013.01); *B01D 29/35* (2013.01); *B29C 49/20* (2013.01); *A61M 2202/0415* (2013.01); *A61M 2207/00* (2013.01); *B04B 5/0442* (2013.01); *B29C 2049/2008* (2013.01); *B29L 2031/753* (2013.01)

(58) Field of Classification Search
CPC .... A61M 2202/0415; A61M 2205/125; A61M 2205/7545; A61M 2207/00; B01D 29/111; B01D 29/35; B04B 5/0442; B29C 2049/2008; B29C 49/20; B29L 2031/753
See application file for complete search history.

(56) References Cited

U.S. PATENT DOCUMENTS

| 8,500,672 B2* | 8/2013 | Caleffi | ............... A61M 1/3627 604/6.09 |
| 2007/0278155 A1* | 12/2007 | Lo | ........................... A61M 1/28 210/646 |
| 2010/0274171 A1 | 10/2010 | Caleffi et al. | |

FOREIGN PATENT DOCUMENTS

| JP | 2003-508170 | 3/2003 |
| JP | 2007-135662 | 6/2007 |
| WO | 200117652 A1 | 3/2001 |
| WO | 2017142003 A1 | 8/2017 |

OTHER PUBLICATIONS

International Searching Authority, International Search Report and Written Opinion, PCT/JP2018/011131, dated Jun. 21, 2018, 10 pages.

* cited by examiner

1

BLOOD COMPONENT COLLECTION CASSETTE AND MANUFACTURING METHOD OF THE SAME

TECHNICAL FIELD

The present invention relates to a blood component collection cassette and a manufacturing method of the same.

BACKGROUND ART

In blood donation in recent years, in addition to whole blood collection where whole blood is collected from a blood donor, blood component collection (apheresis) is performed where load on a body of a blood donor is small. The blood component collection is a method where only specific blood components are collected from whole blood and the residual blood components are returned into the body of the blood donor by using a blood component collection system (apheresis system).

Patent Literature 1 discloses a blood component collection system that collects blood platelets by centrifugally separating whole blood collected from a blood donor. The blood component collection system includes a blood collection circuit set that forms a circuit where blood or blood components to be processed flow and a centrifugal separation device (blood component separation device) to which the blood collection circuit set is mounted.

The blood collection circuit set includes a blood collection line having a blood collection needle, a band-like channel (separator) where whole blood is introduced, a plurality of bags for storing blood components and the like, and a cassette connected to these through a plurality of tubes. In the cassette, a plurality of flow paths are formed which include a line that introduces blood from a blood donor, a line that transfers blood components to the bags, and a blood retransfusion line that returns uncollected blood components to the blood donor. When the cassette is used, the cassette is mounted to a mounting unit provided to the blood component separation device.

CITATION LIST

Patent Literature

[PTL 1]
JP 2013-514863 A

SUMMARY OF INVENTION

Technical Problem

The cassette used for a conventional blood component collection system has a problem that its structure is complicated and its manufacturing cost is high because the cassette is a hard resin molding manufactured by injection molding. Further, a function to trap a substance (aggregate) where blood components coagulate in the circuit is required in the blood retransfusion line so as not to return the substance to the blood donor.

An object of the present invention is to provide a blood component collection cassette that can trap a substance where blood components coagulate by using a simple and economical configuration, and a manufacturing method of the blood component collection cassette.

Solution to Problem

To achieve the above object, the blood component collection cassette includes a cassette main body, where a flow path is formed, and is configured to be mountable to a blood component separation device. The cassette main body is formed of a soft material, and a filter member for trapping a substance where blood components coagulate is arranged on the flow path in the cassette main body.

According to the present invention, the filter member is arranged on the flow path in the cassette main body, so that it is possible to trap a substance where blood components coagulate. The filter member is incorporated in the blood component collection cassette, so that it is not necessary to separately connect a filter mechanism to the blood component collection cassette, and a low-cost merit obtained by using a soft material is not impaired. Further, the filter member is incorporated in the blood component collection cassette, so that an operation to attach a filter mechanism is not required in addition to an operation to mount the blood component collection cassette to the blood component separation device. Therefore, it is possible to improve operability of an operator.

It is preferable that the cassette main body has a filter housing unit that houses the filter member and the filter member is fixed to an inner circumferential portion of the filter housing unit.

It is preferable that the cassette main body has a first sheet and a second sheet which are formed of a soft material, the first sheet and the second sheet are superposed in a thickness direction and bonded to each other, and the flow path is formed between the first sheet and the second sheet. Thereby, the blood component collection cassette can be manufactured by bonding the first sheet and the second sheet which are composed of a soft material, so that the blood component collection cassette can be manufactured at a cost lower than that of a conventional cassette that is manufactured by injection molding and is composed of a hard resin.

It is preferable that an engaging portion attachable to and detachable from a distal end portion of a blow nozzle which is used when the cassette main body is formed by blow molding is provided to the filter member.

By this configuration, when the cassette main body is formed by the blow molding, it is possible to mount the filter member to the distal end portion of the blow nozzle and insert the filter member between base material sheets. Therefore, it is possible to manufacture the blood component collection cassette incorporating the filter member by using a simple and economical method.

An engaging portion attachable to and detachable from a distal end portion of a tool which is used when the cassette main body is formed may be provided to the filter member.

It is preferable that the filter member has a cylindrical filter main body of which one end is provided with an opening portion and of which other end is provided with a bottom portion and the engaging portion protrudes from the other end of the filter main body in a direction opposite to the opening portion.

By this configuration, in a manufacturing process of the blood component collection cassette, it is possible to easily and smoothly pull out the blow nozzle from the filter member and the cassette main body by retreating the blow nozzle after bonding the base material sheets together and forming a flow path by performing the blow molding.

It is preferable that the engaging portion has a plurality of engaging arms provided at intervals in a circumferential direction and an engaging claw protruding inwardly is provided at a free end portion of each of the plurality of engaging arms.

By this configuration, in the manufacturing process of the blood component collection cassette, it is possible to mount the filter member to the distal end portion of the blow nozzle with an appropriate engaging force.

It is preferable that the filter member has a cylindrical filter main body of which one end is provided with an opening portion and of which other end is provided with a bottom portion and on an outer circumferential portion of the filter main body, an annular rib is provided which extends over the entire circumference of the outer circumferential portion and is tightly attached to the cassette main body.

By this configuration, an aggregate is reliably prevented from passing through between the cassette main body and an outer circumferential portion of the filter member, so that it is possible to reliably exert a filter function.

It is preferable that the filter member is formed into a cylindrical shape having a circumferential wall portion of which one end is provided with an opening portion and a bottom portion provided at the other end of the circumferential wall portion, a mesh portion is formed in each of the circumferential wall portion and the bottom portion, and an outer shape of the circumferential wall portion becomes thin as it goes to the bottom portion.

By this configuration, it is possible to cause not only the bottom portion but also the circumferential wall portion to have a filter function, so that an aggregate can be efficiently trapped.

Further, the present invention is a manufacturing method of a blood component collection cassette which includes a cassette main body, where a flow path is formed, and is configured to be mountable to a blood component separation device. The manufacturing method includes an arranging step of arranging a filter member between a first base material sheet and a second base material sheet which are formed of a soft material and, after the arranging step, a bonding/molding step of bonding the first base material sheet and the second base material sheet by sandwiching the first base material sheet, the second base material sheet, and the filter member between molds and performing blow molding so that the flow path where the filter member is arranged is formed.

By the manufacturing method of a blood component collection cassette of the present invention, it is possible to manufacture a blood component collection cassette that can trap an aggregate at a cost lower than that of a conventional cassette that is manufactured by injection molding and is composed of a hard resin.

In the manufacturing method of a blood component collection cassette, it is preferable that the filter member has an engaging portion attachable to and detachable from a distal end portion of a blow nozzle which is used for the blow molding, and the manufacturing method further includes a mounting step of mounting the filter member to the distal end portion of the blow nozzle before the arranging step, and a separating step of separating the blow nozzle from the filter member after the bonding/molding step.

Thereby, it is possible to mount the filter member to the distal end portion of the blow nozzle and insert the filter member between the first and the second base material sheets. Further, it is possible to easily separate the blow nozzle from the filter member by retreating the blow nozzle after the bonding/molding step. Therefore, it is possible to efficiently manufacture the blood component collection cassette incorporating the filter member.

In the manufacturing method of a blood component collection cassette, it is preferable that the blow nozzle has a small-diameter nozzle portion of which diameter is reduced from a nozzle body portion and which extends toward a distal end.

Thereby, it is possible to easily arrange the filter member at a position a predetermined distance away from an outer circumferential portion of the cassette main body.

In the manufacturing method of a blood component collection cassette, it is preferable that an annular convex portion with which the engaging portion of the filter member can engage is provided on a distal-end, outer circumference of the small-diameter nozzle portion.

Thereby, it is possible to mount the filter member to the distal end portion of the blow nozzle with an appropriate engaging force.

Advantageous Effects of Invention

According to the blood component collection cassette and the manufacturing method thereof, it is possible to trap a substance where blood components coagulate by using a simple and economical configuration.

DESCRIPTION OF EMBODIMENTS

Hereinafter, a blood component collection cassette and a manufacturing method of the same related to the present invention will be described using a preferred embodiment with reference to the attached drawings.

Figure 1:
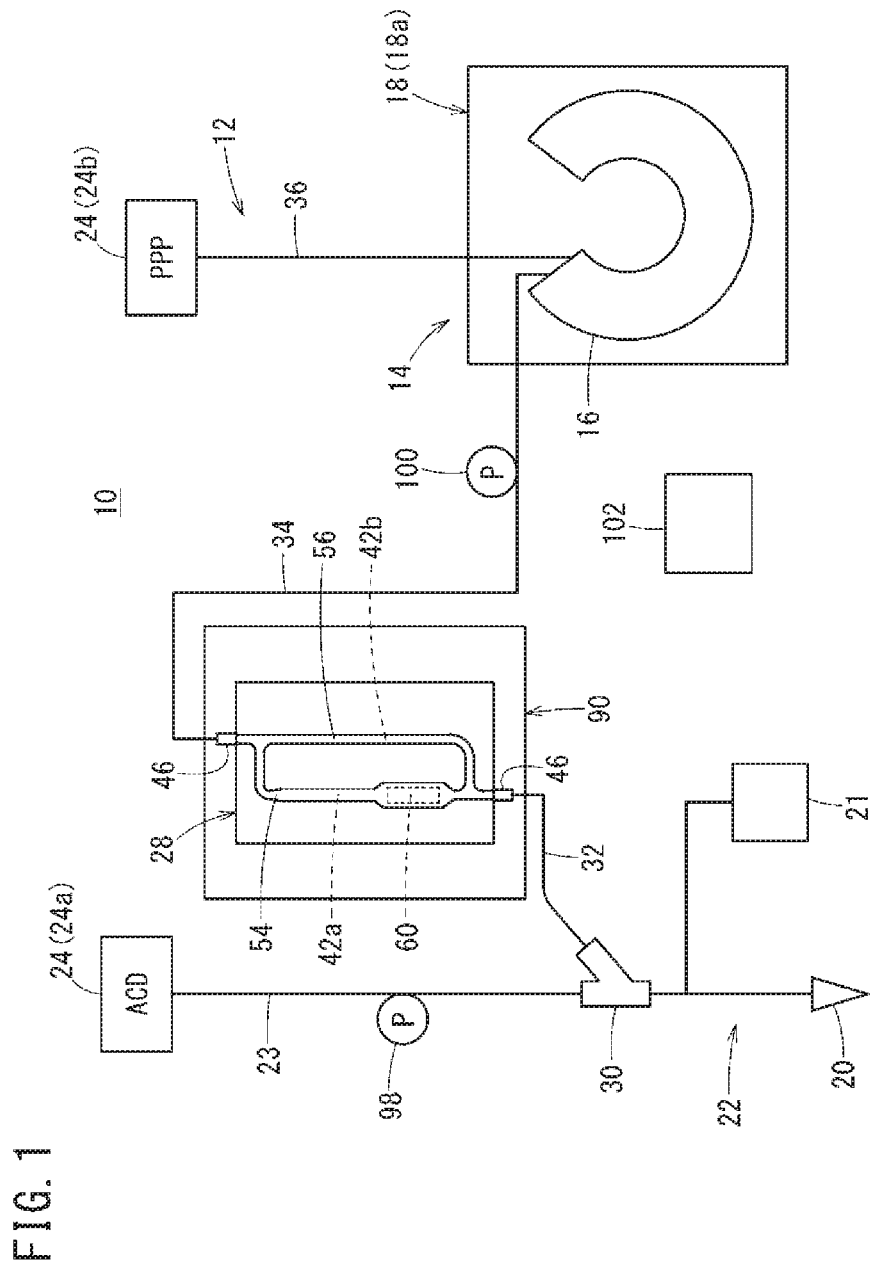
FIG. 1 is a schematic diagram of a blood component collection system related to an embodiment of the present invention.

In FIG. 1, a blood component collection system 10 is configured as a blood apheresis system that collects specific blood components (blood plasma (platelet poor plasma: PPP) in the present embodiment) from a blood donor by continuously extracting blood (whole blood) from the blood donor and centrifugally separating the blood outside the body of the donor and returns the residual blood components to the blood donor.

First, an outline of the blood component collection system 10 shown in FIG. 1 will be described. The blood component collection system 10 includes a blood collection circuit set 12 for storing and flowing blood components and a centrifugal separation device 14 (blood component separation device) that applies a centrifugal force to the blood collection circuit set 12. The blood collection circuit set 12 has a blood treatment unit 16 where the whole blood extracted from the blood donor is introduced and the whole blood is centrifugally separated into a plurality of blood components. The centrifugal separation device 14 includes a centrifugal unit 18 having a rotor 18a for applying a centrifugal force to the blood treatment unit 16. The blood treatment unit 16 is mountable to the centrifugal unit 18.

The blood collection circuit set 12 is disposable for each use in order to prevent contamination and keep hygiene. The blood collection circuit set 12 includes a blood collection/retransfusion unit 22 including a blood collection needle 20 and an initial flow blood collection bag 21, the blood treatment unit 16, a plurality of bags 24, and a blood component collection cassette 28 (hereinafter referred to as a "cassette 28") connected to the above elements through tubes. The plurality of bags 24 include an ACD liquid bag 24a containing ACD liquid that is an anticoagulant and a PPP bag 24b for storing blood plasma (platelet poor plasma).

The blood collection/retransfusion unit 22 is connected to the ACD liquid bag 24a and the cassette 28 through a tube connector 30. The ACD liquid bag 24a is connected to the tube connector 30 through an ACD liquid transfer tube 23.

The cassette 28 is connected to the blood collection/retransfusion unit 22 through a donor side tube 32 and connected to the blood treatment unit 16 through a treatment unit side tube 34. The blood treatment unit 16 is mounted to the centrifugal unit 18 (the rotor 18a) of the centrifugal separation device 14 and is formed into a container shape so that blood is introduced, flows, and flows out. The blood treatment unit 16 is connected with the PPP bag 24b through a PPP transfer tube 36.

Figure 2:
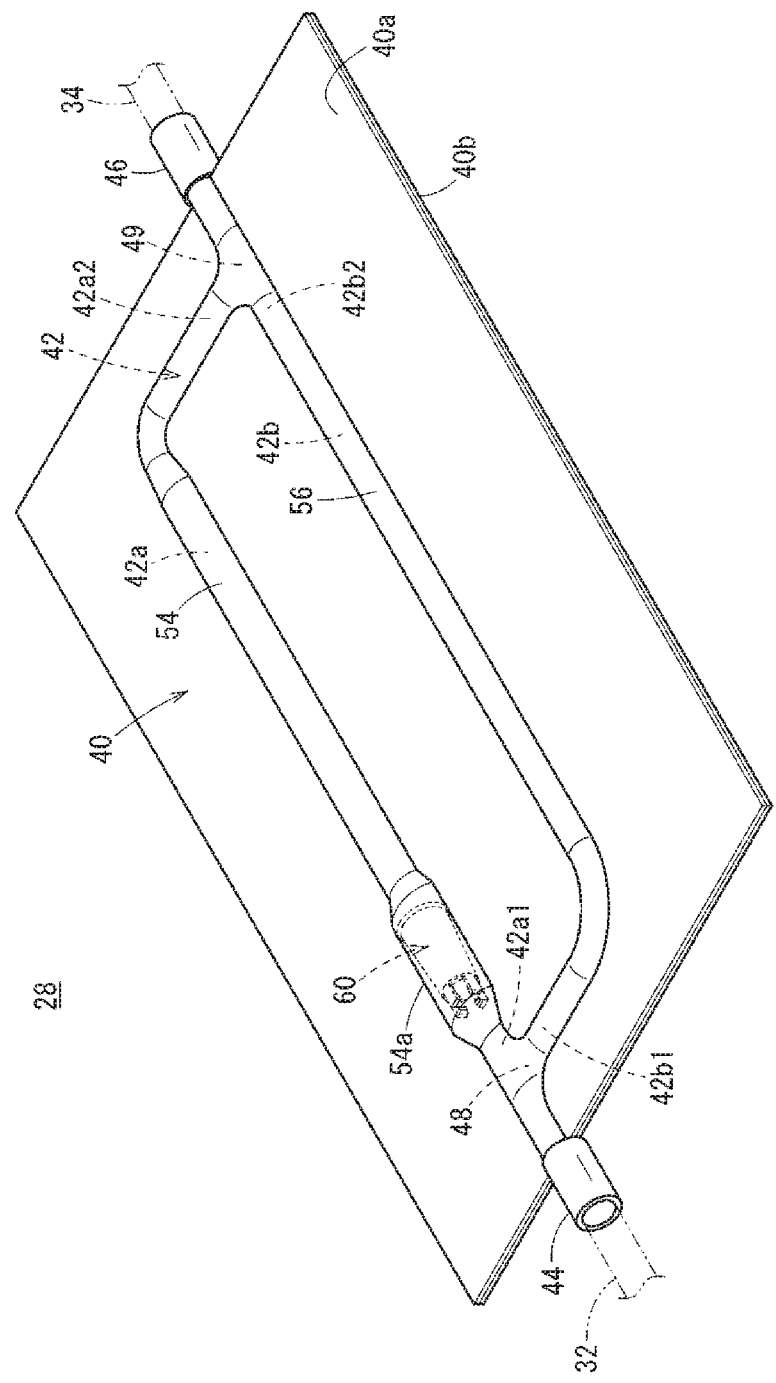
FIG. 2 is a perspective view of a blood component collection cassette.

In FIG. 2, the cassette 28 includes a cassette main body 40 where a flow path 42 is formed. The cassette main body 40 is formed into a rectangular shape in plan view. The cassette main body 40 is formed of a soft material. Specifically, the cassette main body 40 has a first sheet 40a and a second sheet 40b which are formed of a soft material. The first sheet 40a and the second sheet 40b are superposed in a thickness direction and bonded to each other.

Examples of the soft material that forms the first sheet 40a and the second sheet 40b include vinyl chloride, polyolefin, polyurethane, and the like.

The flow path 42 is formed between the first sheet 40a and the second sheet 40b. Examples of a bonding means of the first sheet 40a and the second sheet 40b include welding (high-frequency welding, thermal welding, and the like), adhesion, and the like. A first port member 44 and a second port member 46 are provided to a peripheral portion of the cassette main body 40. The first port member 44 is connected to one end of the flow path 42. The second port member 46 is connected to the other end of the flow path 42. The donor side tube 32 and the treatment unit side tube 34 are connected to these port members 44 and 46, respectively.

The flow path 42 formed in the cassette main body 40 has a first line 42a where a filter member 60 for removing a substance where blood components coagulate (hereinafter referred to as a "blood-coagulated clot") is arranged and a second line 42b where the filter member 60 is not arranged. One end 42a1 of the first line 42a and one end 42b1 of the second line 42b are connected through a first branch portion 48. The other end 42a2 of the first line 42a and the other end 42b2 of the second line 42b are connected through a second branch portion 49. The first line 42a and the second line 42b extend at least partially in parallel with each other. The first branch portion 48 and the second branch portion 49 respectively form parts of the flow path 42.

In the cassette main body 40, a wall portion that forms the flow path 42 convexly protrudes in a thickness direction of the cassette 28 (hereinafter referred to as a "cassette thickness direction") on both surfaces of the cassette main body 40 even when no positive pressure is applied inside the flow path 42. Therefore, the flow path 42 is a flow path that opens in a natural state. When the flow path 42 is pressed by an external force, the flow path 42 can be elastically deformed in a direction in which the flow path 42 is closed at a position where the flow path 42 is pressed. The cassette main body 40 has a convex shaped first line forming wall portion 54 that forms the first line 42a and a convex shaped second line forming wall portion 56 that forms the second line 42b. The first line forming wall portion 54 has a filter housing unit 54a that houses the filter member 60.

Figure 3:
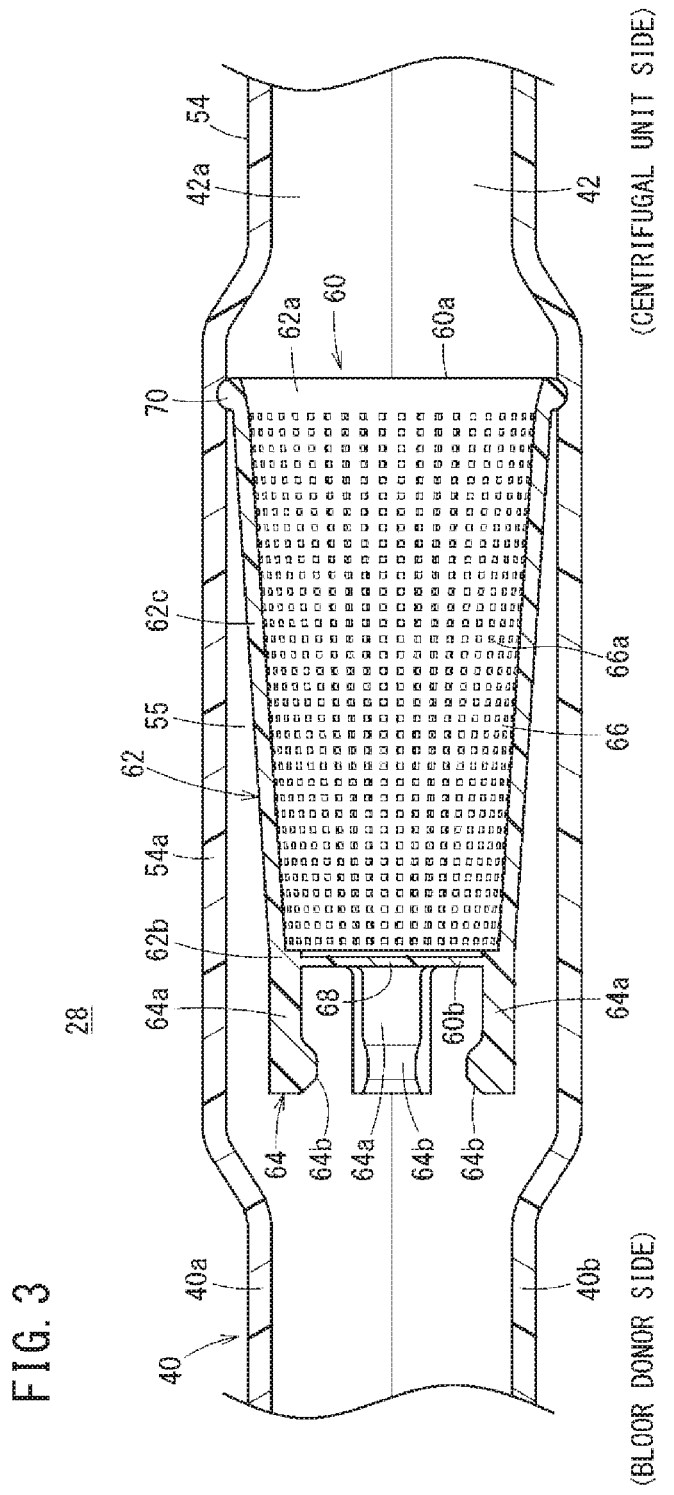
FIG. 3 is a cross-sectional view of the blood component collection cassette.
Figure 4:
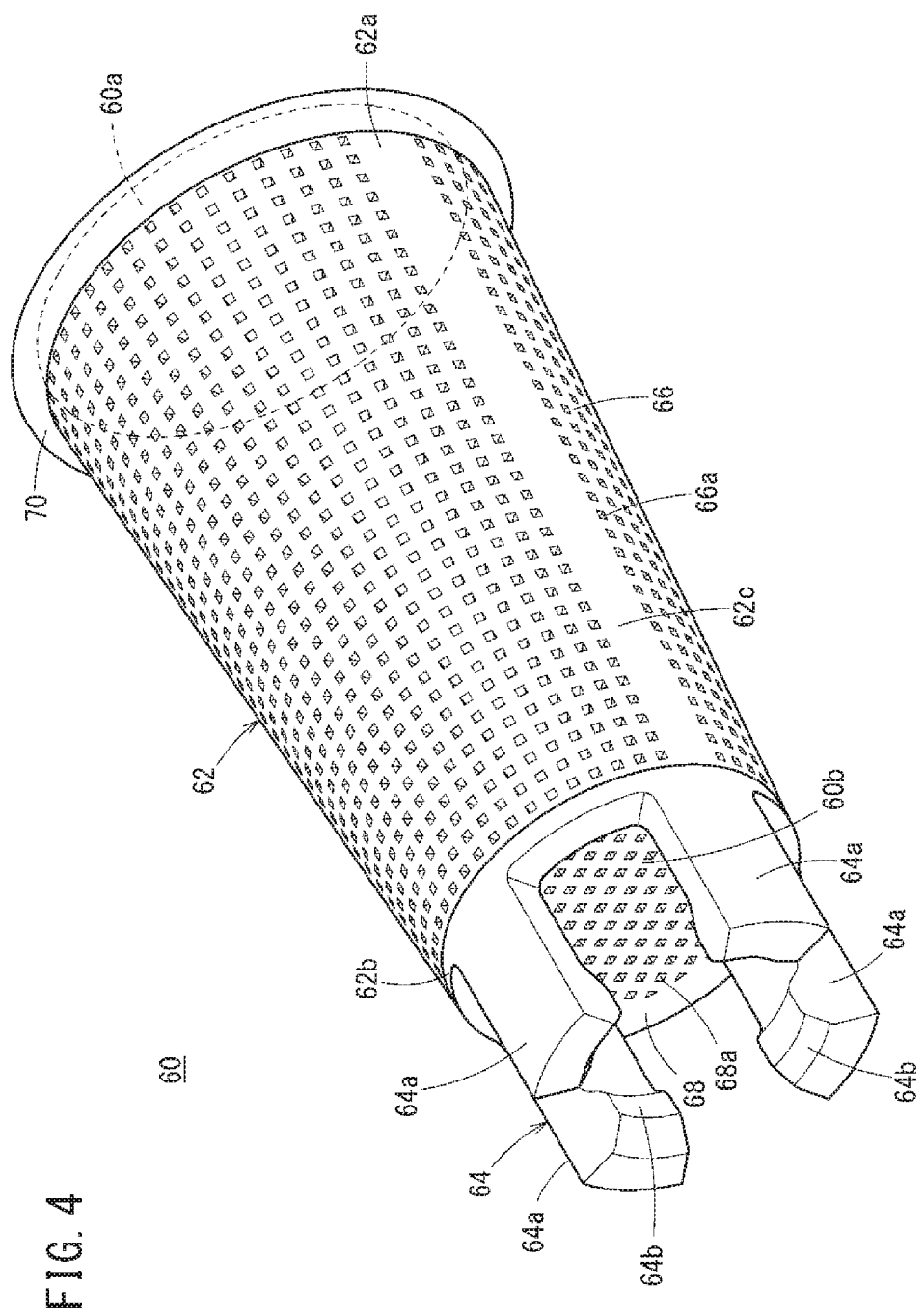
FIG. 4 is a perspective view of a filter member.

As shown in FIGS. 3 and 4, the filter member 60 includes a cylindrical filter main body 62 of which one end 62a is provided with an opening portion 60a and of which other end 62b is provided with a bottom portion 60b and an engaging portion 64 attachable to and detachable from a distal end portion of a blow nozzle 74 (tool) (see FIG. 5) which is used when the cassette main body 40 is formed by blow molding. The filter main body 62 and the engaging portion 64 are integrally formed by, for example, injection molding.

The filter main body 62 has a circumferential wall portion 62c where the opening portion 60a is provided. An outer shape of the circumferential wall portion 62c becomes thin as it goes to the bottom portion 60b. Specifically, in the present embodiment, the filter main body 62 is formed into a truncated cone shape and the outer diameter of the circumferential wall portion 62c is gradually reduced in a tapered form as it goes to the bottom portion 60b.

As shown in FIG. 4, mesh portions 66 and 68 are formed in the circumferential wall portion 62c and the bottom portion 60b, respectively. The mesh portions 66 and 68 are structural portions having a large number of fine holes 66a and 68a having a size where liquid (including blood) is allowed to pass and the blood-coagulated clot can be trapped.

In the mesh portion 66 of the circumferential wall portion 62c, a large number of holes 66a are formed at intervals in an axial direction and a circumferential direction of the filter main body 62 so as to surround an inner space of the circumferential wall portion 62c. The mesh portion 66 is formed in a range from nearby the opening portion 60a to nearby the bottom portion 60b. In the mesh portion 68 of the bottom portion 60b, a large number of holes 68a are formed at intervals in a circumferential direction and a radial direction. The mesh portion 68 is formed over nearly the entire surface of the bottom portion 60b.

As shown in FIG. 3, an annular space 55 is formed between an outer circumferential surface of the mesh portion 66 of the circumferential wall portion 62c and an inner circumferential surface of the filter housing unit 54a. On an outer circumferential portion of the filter main body 62, an annular rib 70 is provided which extends over the entire circumference of the outer circumferential portion and is liquid-tightly attached (fixed) to the first sheet 40a and the second sheet 40b. The annular rib 70 is provided at a largest outer diameter portion of the circumferential wall portion 62c (at the one end 62a that surrounds the opening portion 60a). The annular rib 70 may have a plurality of protrusions that are provided at intervals in the axial direction and protrude outward in the radial direction.

The engaging portion 64 protrudes from the other end 62b of the filter main body 62 in a direction opposite to the opening portion 60a. The engaging portion 64 has a plurality of engaging arms 64a provided at intervals in the circumferential direction. The plurality of engaging arms 64*a* are arranged so as to surround a central axis of the filter main body 62. Each engaging arm 64*a* can be elastically deformed in the radial direction. At a free end portion of each of the plurality of engaging arms 64*a*, an engaging claw 64*b* protruding inwardly is provided.

The filter member 60 is formed of a hard material. Examples of a constituent material of the filter member 60 include vinyl chloride, cyclic polyolefin, polypropylene, polycarbonate, and the like. The filter member 60 may be formed of a metal material.

Figure 5:
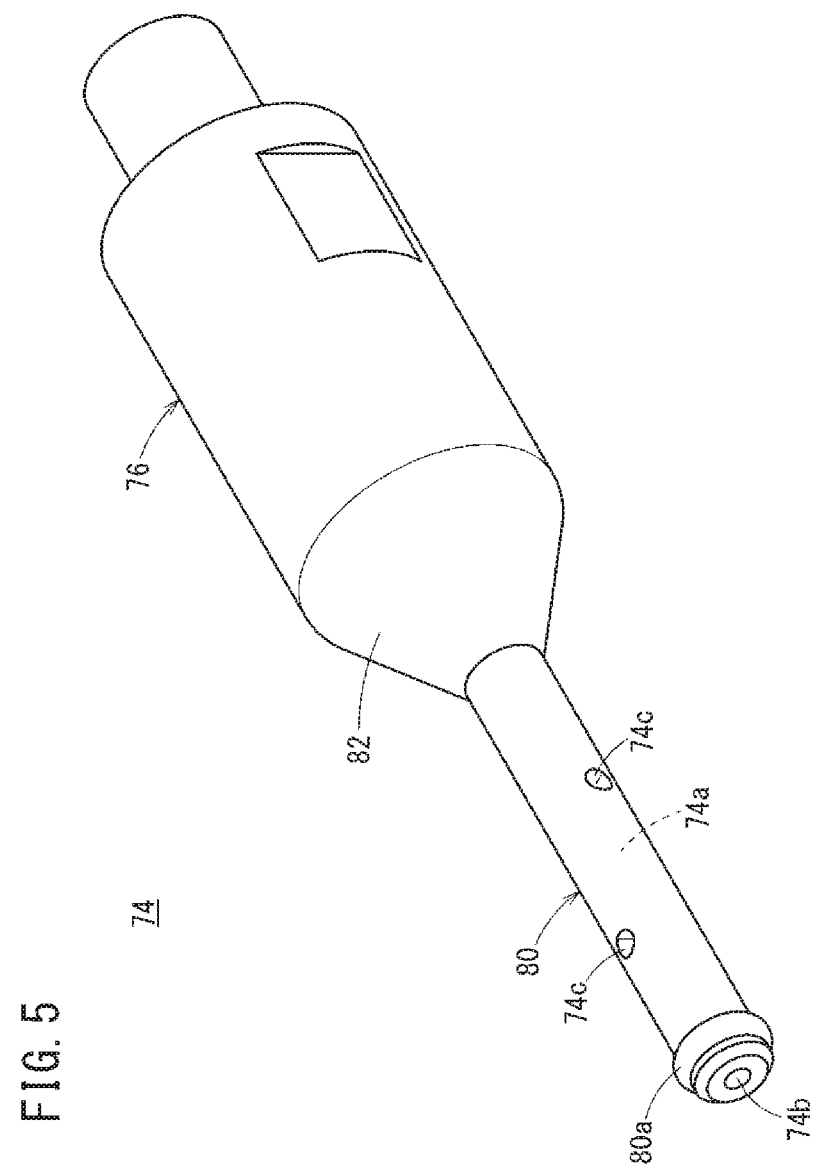
FIG. 5 is a perspective view of a blow nozzle.

As shown in FIG. 5, the blow nozzle 74 has a nozzle body portion 76 and a small-diameter nozzle portion 80 of which diameter is reduced from the nozzle body portion 76 and which extends toward the distal end. An air supply flow path 74*a* (see FIG. 6) is formed inside the blow nozzle 74. The air supply flow path 74*a* is terminated at a distal end opening portion 74*b* provided in a distal end surface of the small-diameter nozzle portion 80. The small-diameter nozzle portion 80 is provided with side holes 74*c* which open in an outer circumferential surface of the small-diameter nozzle portion 80 and communicate with the air supply flow path 74*a*. A plurality of side holes 74*c* are provided. Air for the blow molding is blown out from the distal end opening portion 74*b* and the side holes 74*c*.

A tapered portion 82 of which diameter reduces toward the distal end is provided at a distal end portion of the nozzle body portion 76. The small-diameter nozzle portion 80 linearly extends from the distal end of the tapered portion 82 toward the distal end direction. An annular convex portion 80*a* with which the engaging portion 64 (the plurality of engaging arms 64*a*) (FIG. 4) of the filter member 60 can engage is provided on a distal-end, outer circumference of the small-diameter nozzle portion 80. The outer diameter of the annular convex portion 80*a* is smaller than the outer diameter of the nozzle body portion 76. The side holes 74*c* are provided closer to a base end side (a nozzle body portion 76 side) than the annular convex portion 80*a*.

The cassette 28 having the configuration described above can be manufactured by, for example, the following manufacturing method. The manufacturing method of the cassette 28 according to the present embodiment includes a mounting step (FIG. 6), an arranging step (FIG. 7A), a bonding/molding step (FIG. 7B), a separating step (FIG. 8A), and an extracting step (FIG. 8B).

Figure 6:
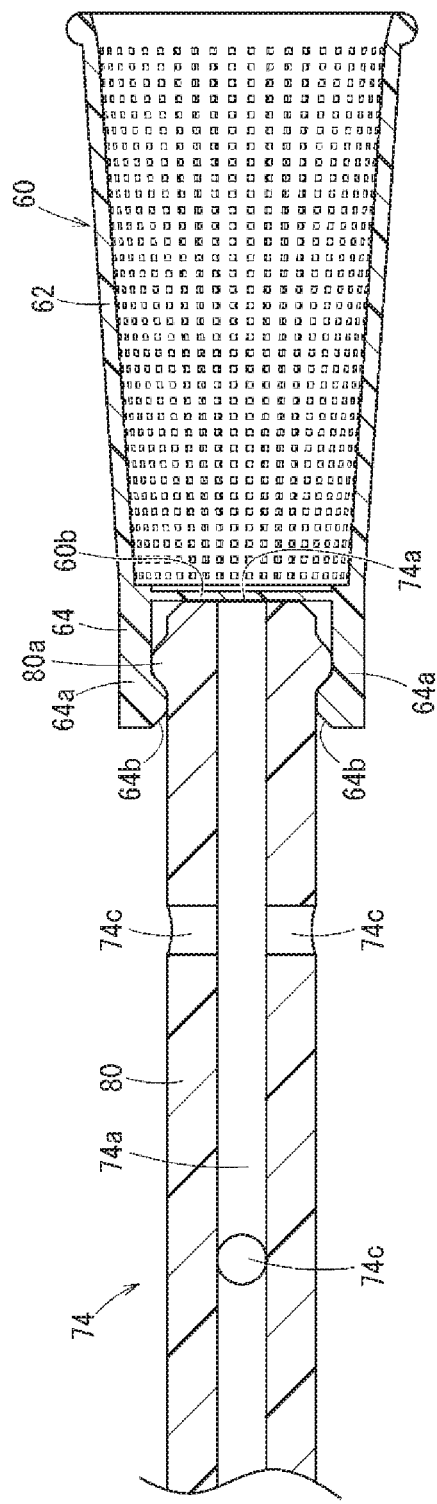
FIG. 6 is a first explanatory diagram of a manufacturing method of the blood component collection cassette.

As shown in FIG. 6, in the mounting step, the filter member 60 is mounted to a distal end portion of the blow nozzle 74. Specifically, the plurality of engaging arms 64*a* of the filter member 60 are fitted to the distal end portion of the blow nozzle 74 from the outside. At this time, the plurality of engaging arms 64*a* are elastically deformed outward in the radial direction, and the engaging claw 64*b* gets over the annular convex portion 80*a* provided on the blow nozzle 74, then the engaging claw 64*b* is hooked on the annular convex portion 80*a*. Thereby, the filter member 60 is held by the distal end portion of the blow nozzle 74. In this state, the distal end surface of the small-diameter nozzle portion 80 comes into contact with or comes close to the bottom portion 60*b* of the filter member 60.

Figure 7A:
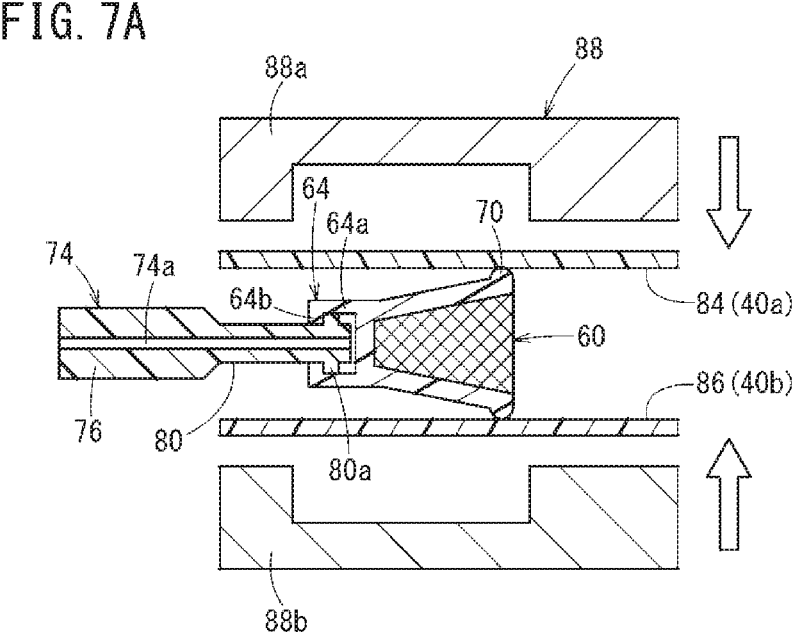
FIG. 7A is a second explanatory diagram of the manufacturing method of the blood component collection cassette.

Next, in the arranging step, as shown in FIG. 7A, the filter member 60 is arranged between a first base material sheet 84 and a second base material sheet 86 which are formed of a soft material. The first base material sheet 84 is a material of the first sheet 40*a* that forms the cassette main body 40. The second base material sheet 86 is a material of the second sheet 40*b*. The first base material sheet 84 and the second base material sheet 86 are arranged in parallel with each other at intervals while facing each other between a pair of molds 88*a* and 88*b* that forms a sheet bonding device 88. The blow nozzle 74 holding the filter member 60 is inserted into a predetermined position between the first base material sheet 84 and the second base material sheet 86 in the above state. In the present embodiment, the sheet bonding device 88 is a high-frequency welding device. The sheet bonding device 88 may be a thermal welding device or the like. In a molding surface of the pair of molds 88*a* and 88*b*, a groove for forming a portion surrounding a flow path of the cassette main body 40 (a convex shaped wall portion) is provided.

Figure 7B:
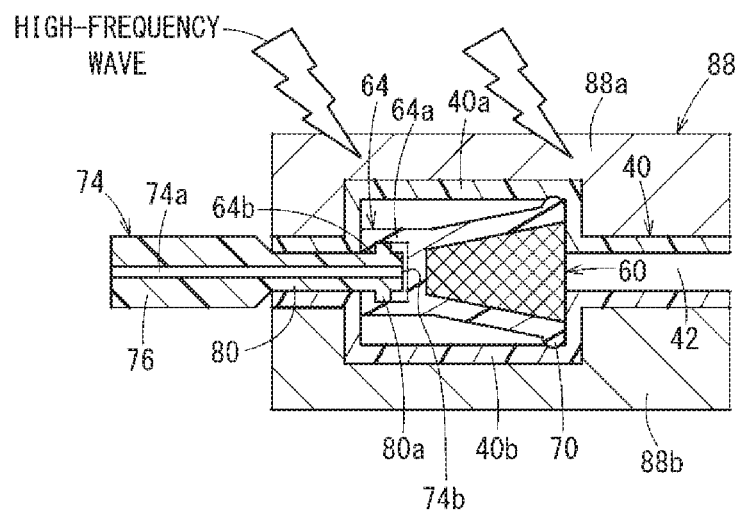
FIG. 7B is a third explanatory diagram of the manufacturing method of the blood component collection cassette.

Next, in the bonding/molding step, as shown in FIG. 7B, the first base material sheet 84 and the second base material sheet 86 are bonded by sandwiching the first base material sheet 84, the second base material sheet 86, and the filter member 60 between the molds 88*a* and 88*b*, and the blow molding is performed so that the flow path 42 where the filter member 60 is arranged is formed.

Specifically, the pair of molds 88*a* and 88*b* is closed, the first base material sheet 84 and the second base material sheet 86 are superposed, and predetermined portions of the first base material sheet 84 and the second base material sheet 86 are high-frequency welded so as to form the flow path 42. At this time, the flow path 42 is formed by blowing air from the blow nozzle 74 and inflating a portion corresponding to the groove provided to the molds 88*a* and 88*b* in the first base material sheet 84 and the second base material sheet 86.

The air is blown out from the distal end opening portion 74*b* and the side holes 74*c* (FIG. 5) of the blow nozzle 74. The air blown out from the distal end opening portion 74*b* passes through the mesh portion 68 (FIG. 4) provided to the bottom portion 60*b* of the filter member 60, so that the air is reliably supplied beyond the filter member 60. Thereby, the cassette main body 40 is formed which has the first sheet 40*a* and the second sheet 40*b* that are bonded to each other and in which the flow path 42 is formed and the filter member 60 is incorporated.

Figure 8A:
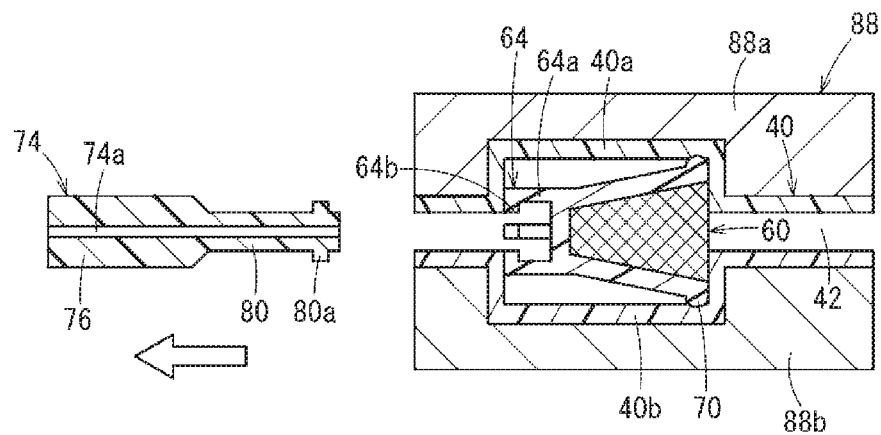
FIG. 8A is a fourth explanatory diagram of the manufacturing method of the blood component collection cassette.
Figure 8B:
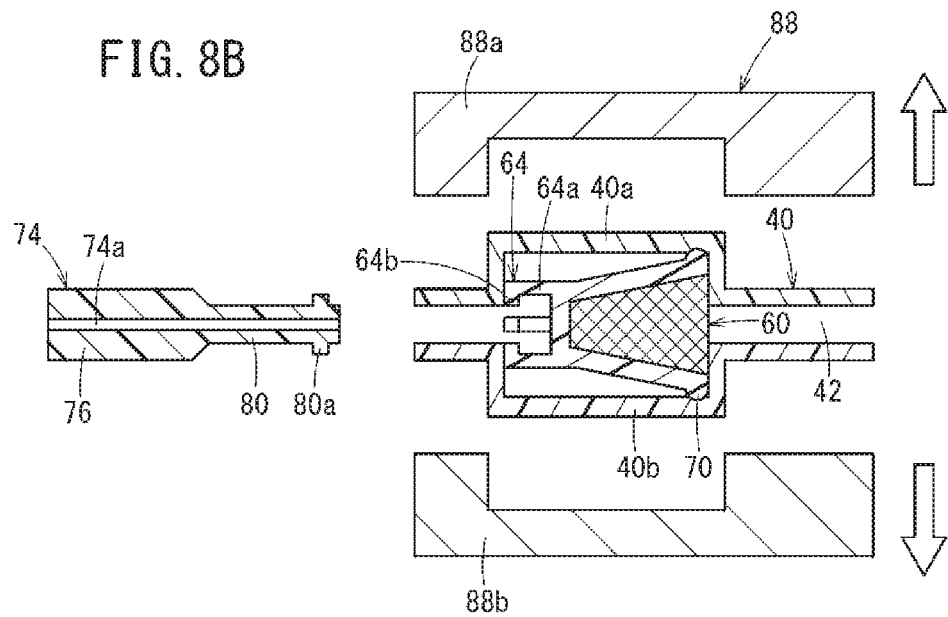
FIG. 8B is a fifth explanatory diagram of the manufacturing method of the blood component collection cassette.

Next, in the separating step, as shown in FIG. 8A, the blow nozzle 74 is separated from the filter member 60. Specifically, when the blow nozzle 74 is retreated in a state in which the pair of molds 88*a* and 88*b* is closed, engagement between the annular convex portion 80*a* of the blow nozzle 74 and the engaging portion 64 of the filter member 60 is released, and the blow nozzle 74 is pulled out from the cassette main body 40 and the filter member 60.

Next, in the extracting step, as shown in FIG. 8B, the pair of molds 88*a* and 88*b* is opened and the cassette main body 40, which is a molded article, is extracted.

In FIG. 1, the centrifugal separation device 14 is an apparatus that is repeatedly used to collect blood components, and for example, the centrifugal separation device 14 is installed in a medical facility, a bloodmobile, and the like. The centrifugal separation device 14 includes the centrifugal unit 18 having the rotor 18*a* and a cassette mounting unit 90 configured so that the cassette 28 of the blood collection circuit set 12 can be mounted.

Although details are not shown in the drawings, the cassette mounting unit 90 is provided with a first clamp and a second clamp which can respectively and individually press the first line forming wall portion 54 and the second line forming wall portion 56 of the cassette 28. Each clamp can advance and retract in a thickness direction of the cassette held by the cassette mounting unit 90 and is arranged corresponding to arrangement of the first line forming wall portion 54 and the second line forming wall portion 56 provided in the cassette 28.

In a state in which the cassette 28 is mounted in the cassette mounting unit 90, when the first line forming wall portion 54 and the second line forming wall portion 56 are not pressed by the first clamp and the second clamp, respectively, the first line 42a and the second line 42b are released, respectively. When the first clamp and the second clamp press the first line forming wall portion 54 and the second line forming wall portion 56, respectively, the first line 42a and the second line 42b are closed, respectively. When the first clamp and the second clamp retreat, respectively, the first line 42a and the second line 42b are opened by an elastic restoring force of the first line forming wall portion 54 and the second line forming wall portion 56.

As shown in FIG. 1, the centrifugal separation device 14 has an ACD liquid transfer pump 98 that acts on the ACD liquid transfer tube 23 and a blood collection/retransfusion pump 100 that acts on the treatment unit side tube 34 connected to the cassette 28. The ACD liquid transfer pump 98 is a pump that transfers the ACD liquid from the ACD liquid bag to the cassette 28 and the blood treatment unit 16 through the ACD liquid transfer tube. The blood collection/retransfusion pump 100 is a pump that transfers blood from a blood donor to the blood treatment unit 16 and transfers blood from the blood treatment unit 16 to the blood donor. The ACD liquid transfer pump 98 and the blood collection/retransfusion pump 100 are configured by, for example, a roller pump or a finger pump.

The centrifugal separation device 14 further has a control unit 102 that controls the centrifugal unit 18, the cassette mounting unit 90, and the pumps 98 and 100. Operations of the first clamp and the second clamp described above are controlled by the control unit 102.

As a preparation (setup) for collecting blood components from a blood donor by using the blood component collection system 10 shown in FIG. 1, the blood collection circuit set 12 is mounted to the centrifugal separation device 14. Specifically, the cassette 28 is attached to the cassette mounting unit 90 and the blood treatment unit 16 is mounted to the rotor 18a. On the other hand, the blood collection needle 20 is punctured into the blood donor.

When an operation start is instructed to the centrifugal separation device 14 shown in FIG. 1 by an operation of a user, in the centrifugal separation device 14, priming by the ACD liquid is performed under the action of the ACD liquid transfer pump 98. Specifically, in the priming, the ACD liquid is introduced from the ACD liquid bag 24a to the flow path 42 in the cassette 28 through the ACD liquid transfer tube 23, and when a line sensor (not shown in the drawings) on the flow path 42 detects that the ACD liquid comes immediately close to the first line 42a, the priming by the ACD liquid is completed.

Next, the centrifugal separation device 14 applies a centrifugal force to the blood treatment unit 16 mounted to the rotor 18a by rotating the rotor 18a, and extracts blood (whole blood) from the blood donor and introduces the blood into the blood treatment unit 16 by operating the blood collection/retransfusion pump 100 (blood collection operation). The blood introduced into the blood treatment unit 16 is separated into red blood cells (packed red blood cells), buffy coat, and blood plasma (platelet poor plasma) by a centrifugal force due to the rotation of the rotor 18a.

The blood plasma separated in the blood treatment unit 16 is introduced to the PPP bag 24b through the PPP transfer tube 36. The residual blood components (red blood cells and buffy coat) are returned to the blood donor after the centrifugal separation treatment (retransfusion operation). At this time, in the retransfusion operation, the aforementioned second clamp of the cassette mounting unit 90 is closed, and thereby the second line 42b is closed. Therefore, the blood components pass through only the first line 42a instead of both the first and the second lines 42a and 42b. Thereby, a blood-coagulated clot included in the residual blood components is trapped by the filter member 60 while the blood-coagulated clot passes through the first line 42a. Therefore, it is possible to reduce a risk caused by a blood-coagulated clot returning to the blood donor. The blood collection operation and the retransfusion operation described above are repeated a plurality of times.

In this case, the blood component collection system 10 according to the present embodiment has effects described below.

According to the cassette 28, the filter member 60 is arranged on the flow path 42 in the cassette main body 40, so that it is possible to trap the blood-coagulated clot included in the blood components to be returned to the blood donor. The filter member 60 is incorporated in the cassette 28, so that it is not necessary to separately connect a filter mechanism to the cassette 28, and the low-cost merit obtained by using a soft material is not impaired. Further, the filter member 60 is incorporated in the cassette 28, so that an operation to attach a filter mechanism is not required in addition to an operation to mount the cassette 28 to the centrifugal separation device 14. Therefore, it is possible to improve operability of an operator.

The cassette 28 can be manufactured at a cost lower than that of a conventional cassette that is manufactured by injection molding and is composed of a hard resin because the cassette main body 40 is obtained by welding the first sheet 40a and the second sheet 40b which are composed of a soft material.

As shown in FIG. 6, the engaging portion 64 attachable to and detachable from the distal end portion of a blow nozzle 74 which is used when the cassette main body 40 is formed by blow molding is provided to the filter member 60. By this configuration, when forming the cassette main body 40 by the blow molding, it is possible to mount the filter member 60 to the distal end portion of the blow nozzle 74 and insert the filter member 60 between the base material sheets 84 and 86 (FIG. 7A). Therefore, it is possible to manufacture the cassette 28 incorporating the filter member 60 by using a simple and economical method.

The filter member 60 has the cylindrical filter main body 62 of which one end 62a is provided with the opening portion 60a and of which other end 62b is provided with the bottom portion 60b. The engaging portion 64 protrudes from the other end 62b of the filter main body 62 in a direction opposite to the opening portion 60a. By this configuration, in the manufacturing process of the cassette 28, it is possible to easily and smoothly pull out the blow nozzle 74 from the filter member 60 and the cassette main body 40 by retreating the blow nozzle 74 after bonding the base material sheets 84 and 86 together and forming the flow path 42 by performing the blow molding (FIG. 8A).

The engaging portion 64 has a plurality of engaging arms 64a provided at intervals in the circumferential direction. At the free end portion of each of the plurality of engaging arms 64a, the engaging claw 64b protruding inwardly is provided. By this configuration, in the manufacturing process of the cassette 28, it is possible to mount the filter member 60 to the distal end portion of the blow nozzle 74 with an appropriate engaging force.

On the outer circumferential portion of the filter main body 62, the annular rib 70 is provided which extends over the entire circumference of the outer circumferential portion and is tightly attached to the first sheet 40*a* and the second sheet 40*b*. By this configuration, a blood-coagulated clot is reliably prevented from passing through between the first and the second sheets 40*a* and 40*b* and the outer circumferential portion of the filter member 60, so that it is possible to reliably exert a filter function.

As shown in FIG. 3, the filter member 60 is formed into a cylindrical shape having the circumferential wall portion 62*c* of which one end is provided with the opening portion 60*a* and the bottom portion 60*b* provided at the other end of the circumferential wall portion 62*c*. The mesh portions 66 and 68 are formed in the circumferential wall portion 62*c* and the bottom portion 60*b*, respectively. The outer shape of the circumferential wall portion 62*c* becomes thin as it goes to the bottom portion 60*b*. By this configuration, it is possible to cause not only the bottom portion 60*b* but also the circumferential wall portion 62*c* to have a filter function, so that the blood-coagulated clots can be efficiently trapped.

The manufacturing method of the cassette 28 according to the present embodiment includes the arranging step (FIG. 7A) of arranging the filter member 60 between the first base material sheet 84 and the second base material sheet 86 which are formed of a soft material and, after the arranging step, the bonding/molding step (FIG. 7B) of bonding the first base material sheet 84 and the second base material sheet 86 by sandwiching the first base material sheet 84, the second base material sheet 86, and the filter member 60 between the molds 88*a* and 88*b* and performing the blow molding so that the flow path 42 where the filter member 60 is arranged is formed.

By this manufacturing method, it is possible to manufacture the cassette 28 that can trap the blood-coagulated clot included in the blood components to be returned to the blood donor at a cost lower than that of a conventional cassette that is manufactured by injection molding and is composed of a hard resin.

The filter member 60 has the engaging portion 64 attachable to and detachable from the distal end portion of the blow nozzle 74 which is used for the blow molding. The manufacturing method of the cassette 28 includes the mounting step (FIG. 6) of mounting the filter member 60 to the distal end portion of the blow nozzle 74 before the arranging step, and the separating step (FIG. 8A) of separating the blow nozzle 74 from the filter member 60 after the bonding/molding step.

Thereby, it is possible to mount the filter member 60 to the distal end portion of the blow nozzle 74 and easily insert the filter member 60 between the first and the second base material sheets 84 and 86. Further, it is possible to easily separate the blow nozzle 74 from the filter member 60 by retreating the blow nozzle 74 after the bonding/molding step. Therefore, it is possible to efficiently manufacture the cassette 28 incorporating the filter member 60.

The blow nozzle 74 has the small-diameter nozzle portion 80 of which diameter is reduced from the nozzle body portion 76 and which extends toward the distal end. Thereby, in the arranging step (FIG. 7A), it is possible to easily arrange the filter member 60 at a position a predetermined distance away from an outer circumferential portion of the cassette main body 40.

The annular convex portion 80*a* with which the engaging portion 64 of the filter member 60 can engage is provided on the distal-end, outer circumference of the small-diameter nozzle portion 80. Thereby, it is possible to mount the filter member 60 to the distal end portion of the blow nozzle 74 with an appropriate engaging force.

In the cassette 28 described above, the flow path 42 is formed between the first sheet 40*a* and the second sheet 40*b* which are formed of a soft material. However, a structure where the flow path 42 is formed is not limited to such a configuration. For example, a member that forms the flow path 42 in the cassette main body may be a tube.

The cassette main body may be formed by a molding method other than the blow molding (for example, insert molding).

In this case, an engaging portion attachable to and detachable from a distal end portion of a tool which is used when the cassette main body is formed may be provided to the filter member 60.

The present invention is not limited to the embodiment described above, but can be variously changed without departing from the scope of the invention.

REFERENCE SIGNS LIST

10 Blood component collection system
14 Centrifugal separation device
40 Cassette main body
40*a* First sheet
40*b* Second sheet
42 Flow path
60 Filter member
64 Engaging portion
64*a* Engaging arm
74 Blow nozzle

The invention claimed is:

1. A blood component collection cassette, comprising:
   a cassette main body, including a flow path, the cassette main body being mountable to a blood component separation device, wherein the cassette main body includes a first sheet formed of a soft material and a second sheet formed of the soft material and bonded to one another; and
   a filter member for trapping a substance where blood components coagulate in the flow path in the cassette main body,
   wherein the filter member has a cylindrically shaped filter main body,
   wherein an outer circumferential portion of the filter main body includes an annular rib, and
   wherein the first sheet and the second sheet each include a portion that conforms to the annular rib to provide a liquid-tight seal between the first and second sheets and the annular rib.

2. The blood component collection cassette according to claim 1, wherein
   the annular rib is located in an inner circumferential portion of a filter housing section that houses the filter member.

3. The blood component collection cassette according to claim 1, wherein
   the flow path is formed between the first sheet and the second sheet.

4. The blood component collection cassette according to claim 3, wherein
   the filter member comprises an engaging portion attachable to and detachable from a distal end portion of a blow nozzle used when the cassette main body is blow-molded.

5. The blood component collection cassette according to claim 1, wherein
the filter member comprises an engaging portion attachable to and detachable from a distal end portion of a tool used when the cassette main body is formed.

6. The blood component collection cassette according to claim 4, wherein
the filter member has one end provided with an opening portion and another end provided with a bottom portion, and
the engaging portion protrudes from the one end of the filter main body and extends in in a direction that is away from the opening portion.

7. The blood component collection cassette according to claim 6, wherein
the engaging portion includes a plurality of engaging arms provided at intervals in a circumferential direction, and
an engaging claw protruding inwardly is provided at a free end portion of each of the plurality of engaging arms.

8. The blood component collection cassette according to claim 1, wherein the annular rib is at one end of the filter main body.

9. The blood component collection cassette according to claim 1, wherein
the filter main body includes a circumferential wall portion having one end provided with an opening portion and another end provided with a bottom portion,
a mesh portion is formed in each of the circumferential wall portion and the bottom portion, and
an outer shape of the circumferential wall portion tapers inward toward the bottom portion.

10. The blood component collection cassette according to claim 2, wherein
the flow path is formed between the first sheet and the second sheet.

11. The blood component collection cassette according to claim 2, wherein
the filter member includes an engaging portion attachable to and detachable from a distal end portion of a tool used when the cassette main body is formed.

12. The blood component collection cassette according to claim 11, wherein
the filter main body includes one end provided with an opening portion and another end provided with a bottom portion, and
the engaging portion protrudes from the one end of the filter main body and extends in a direction that is away from the opening portion.

13. The blood component collection cassette according to claim 5, wherein
the filter main body includes one end provided with an opening portion and another end provided with a bottom portion, and
the engaging portion protrudes from the one end of the filter main body and extends in a direction that is away from the opening portion.

14. A blood component collection system, comprising:
a blood component separation device; and
a blood component collection cassette, including:
a cassette main body including a flow path, the cassette main body being mountable to the blood component separation device, wherein the cassette main body includes a first sheet formed of a soft material and a second sheet formed of the soft material and bonded to one another; and
a filter member for trapping a substance where blood components coagulate in the flow path in the cassette main body,
wherein the cassette main body includes a filter housing section that houses the filter member,
wherein the filter member has a cylindrically shaped filter main body,
wherein an outer circumferential portion of the filter main body includes an annular rib, and
wherein the first sheet and the second sheet each include a portion that conforms to the annular rib to provide a liquid-tight seal between the first and second sheets and the annular rib.

15. The blood component collection system according to claim 14, wherein
the flow path is formed between the first sheet and the second sheet.

16. The blood component collection system according to claim 15, wherein
the filter member comprises an engaging portion attachable to and detachable from a distal end portion of a blow nozzle used when the cassette main body is blow-molded.

17. The blood component collection system according to claim 14, wherein
the filter member comprises an engaging portion attachable to and detachable from a distal end portion of a tool used when the cassette main body is formed.

18. The blood component collection system according to claim 17, wherein
the filter member has one end provided with an opening portion and another end provided with a bottom portion, and
the engaging portion protrudes from the one end of the filter main body and extends in in a direction that is away from the opening portion.

19. The blood component collection system according to claim 18, wherein
the engaging portion includes a plurality of engaging arms provided at intervals in a circumferential direction, and
an engaging claw protruding inwardly is provided at a free end portion of each of the plurality of engaging arms.

20. The blood component collection system according to claim 14, wherein the annular rib is at one end of the filter main body.

* * * * *